United States Patent [19]

Cale, Jr. et al.

[11] 4,260,606
[45] Apr. 7, 1981

[54] 3-METHYLENEAZETIDINE DERIVATIVES

[75] Inventors: Albert D. Cale, Jr., Mechanicsville, Va.; Herndon Jenkins, Atlanta, Ga.

[73] Assignee: A. H. Robins Company, Inc., Richmond, Va.

[21] Appl. No.: 59,093

[22] Filed: Jul. 19, 1979

[51] Int. Cl.$^3$ .................. C07D 205/08; A61K 31/395
[52] U.S. Cl. .................. 424/244; 260/239 A
[58] Field of Search .................. 260/239 AR; 424/244

[56] References Cited

U.S. PATENT DOCUMENTS

| | | | |
|---|---|---|---|
| 3,458,635 | 7/1969 | Lunsford | 424/274 |
| 3,481,920 | 12/1969 | Hargrove | 260/239 A |
| 3,494,964 | 2/1970 | Hargrove | 260/239 A |
| 3,732,247 | 5/1973 | Helsley | 424/274 |
| 4,065,573 | 12/1977 | Lednicer | 260/239 A |
| 4,078,072 | 3/1978 | Melloni et al. | 260/239 A |
| 4,078,073 | 3/1978 | Melloni et al. | 260/239 A |
| 4,118,499 | 10/1978 | Stephenson | 260/239 A |

OTHER PUBLICATIONS

Morimoto et al., Chem. Abst. 78, 135964y, (1973).

*Primary Examiner*—Mark L. Berch

[57] ABSTRACT

This invention provides a novel class of 3-methyleneazetidines which include diphenylmethyl derivatives such as 1-isopropyl-3-diphenylmethyleneazetidine oxalate:

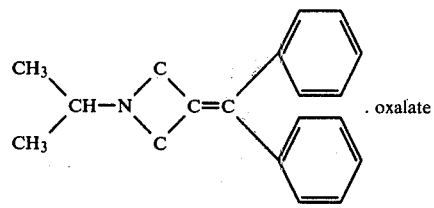

This illustrated 3-methyleneazetidine compound is characterized by a combination of pharmacological properties which are indicative of utility as a mood elevating therapeutic agent for relieving the symptoms of depression in humans. The illustrated compound exhibits an ED$_{50}$ (tetrabenazine-induced ptosis) of 2.18 mg/kg in mice.

9 Claims, No Drawings

3-METHYLENEAZETIDINE DERIVATIVES

BACKGROUND OF THE INVENTION

Of general background interest in connection with the present invention are prior art compounds such as α-(1-R-3-pyrrolidinyl)-α,α-diphenylacetamides (and -acetonitriles) and α-(1-R-3-pyrrolidinyl)-α-phenyl-α-(2-pyridyl)acetamides (and -acetonitriles) which are disclosed in U.S. Pat. Nos. 3,192,206; 3,192,210; 3,192,221; 3,102,230; and 4,002,766.

Also of interest are the anti-depressant 3-disubstituted methylene pyrrolidines disclosed in U.S. Pat. No. 3,732,247:

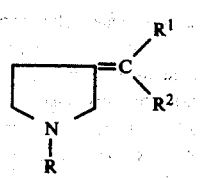

wherein R is selected from the grop consisting of hydrogen, lower-alkyl, phenyl-lower-alkyl, substituted phenyl-lower-alkyl, cycloalkyl, phenoxy-lower-alkyl, phenylamino-lower-alkyl, and substituted phenyl, said lower-alkyl being limited to contain 2 to 8 carbon atoms when $R^1$ and $R^2$ are both phenyl; $R^1$ is selected from the group consisting of lower-alkyl, phenyl-lower-alkyl, cycloalkyl, phenyl and substituted phenyl; and $R^2$ is selected from the group consisting of phenyl and substituted phenyl.

U.S. Pat. No. 4,133,881 discloses a class of α-(1-R-3-azetidinyl)-α-phenyl-α-substituted-acetamides and -acetonitriles corresponding to the following formula:

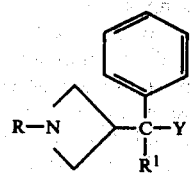

wherein R represents hydrogen, lower alkyl, lower cycloalkyl or phenyl-lower alkyl, $R^1$ represents phenyl or 2-pyridyl, and Y is carbamoyl or cyano, which compounds exhibit antiarrhythmic activity.

Accordingly, it is a main object of the present invention to provide a novel class of 3-methyleneazetidine compounds which are characterized by one or more pharmacological properties useful for counteracting specific physiological abnormalities in humans and other mammals.

Other objects and advantages shall become apparent from the accompanying description and examples.

DESCRIPTION OF THE INVENTION

One or more objects of the present invention are accomplished by the provision of a novel class of pharmacologically active 3-methyleneazetidine derivatives. Illustrative of the organic derivatives is a 3-methyleneazetidine compound corresponding to the formula:

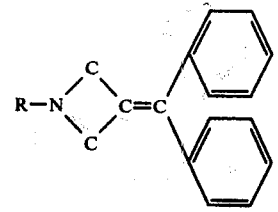

wherein R is a lower-alkyl, cycloalkyl or phenyl-lower-alkyl radical.

The present invention also contemplates the pharmaceutically acceptable acid addition salts of the novel class of 3-methyleneazetidine derivatives. Such salts have improved water solubility over the free bases. Typical acid addition salts are those derived from mineral acids such as hydrochloric, hydrobromic, sulfuric and phosphoric; and organic acids such as acetic, citric, lactic, maleic, oxalic, fumaric and tartaric. The acid addition salts are conveniently prepared by reaction of the basic compounds with the selected acid, either or both of which may be in the form of ether, alcohol or acetone solutions.

The above described novel class of 3-methyleneazetidine compounds, and particularly the acid addition salts thereof, are characterized by useful pharmacological activity, which is indicative of their application in counteracting certain physiological abnormalities in humans. The invention 3-methyleneazetidine compounds possess a significant level of antidepressant activity, such as is observed in reserpine reversal and anti-tetrabenazine tests.

In the above represented structural formula, the lower-alkyl moiety contains between 1 and about 8 carbon atoms, e.g., methyl, ethyl, propyl, isopropyl, butyl, pentyl, hexyl, octyl, and the like.

The cycloalkyl moiety as designated in the structural formula is preferably a cyclic radical containing between 3 and 9 ring carbon atoms, e.g., cyclopropyl, cyclobutyl, cyclopentyl, cyclohexyl, cycloheptyl, cyclooctyl, and the like.

Representative of phenyl-lower-alkyl radicals are α-methylbenzyl, phenylethyl, phenylpropyl, phenylbutyl, and the like.

Illustrative of specific 3-methylazetidine compounds in accordance with the present invention are 1-methyl-3-diphenylmethyleneazetidine, 1-ethyl-3-diphenylmethyleneazetidine, 1-isopropyl-3-diphenylmethyleneazetidine, 1-cyclohexyl-3-diphenyleneazitidine, 1-(α-methylbenzyl)-3-diphenylmethyleneazetidine, and pharmaceutically acceptable acid addition salts thereof.

Preparation of 3-Methyleneazetidines

The invention 3-methyleneazetidine compounds are conveniently prepared by a synthesis procedure which is illustrated by the following reaction sequence:

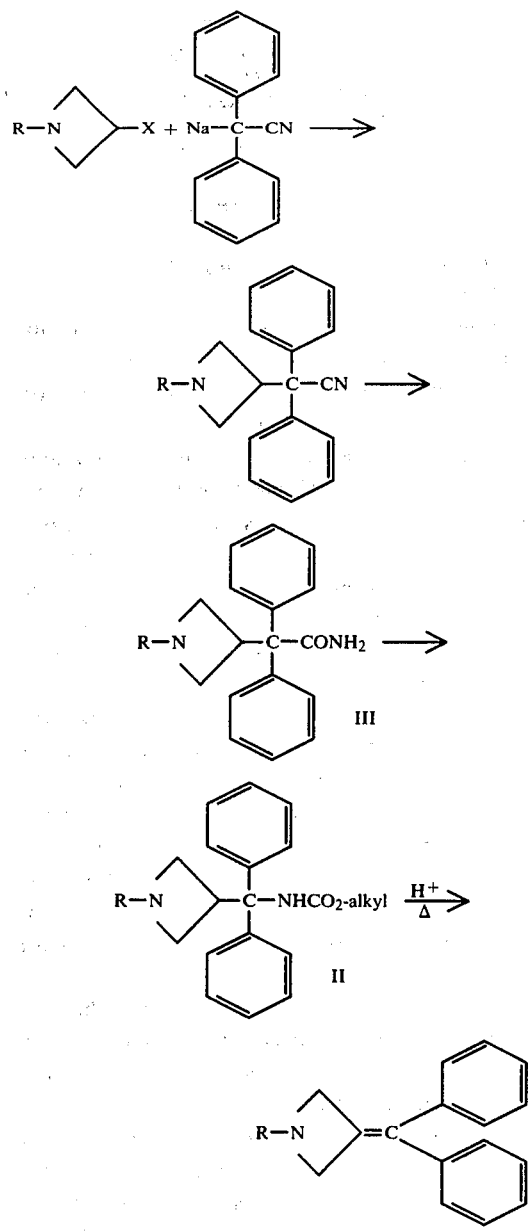

wherein R is alkyl, cycloalkyl or phenyl-lower-alkyl, and X is preferably a halo or sulfonato substitutent.

The preparation of 1-substituted-3-azetidinols and other 1,3-disubstituted azetidine derivatives are described in Tetrahedron Letters, No. 39, 4691 (1966); Tetrahedron Letters, No. 23, 2155 (1967); J. Org. Chem., 32, 2972 (1967); Chem. Pharm. Bull. 22, 1490 (1974); and German Offen. 1.932.219.

In the above illustrated reaction sequence flow diagram, the α,α-diphenylacetonitrile is first metalated in a dry aprotic solvent employing sodium hydride or sodamide to provide sodio α,α-diphenylacetonitrile, which is reacted with a selected 1-R-3-mesyloxyazetidine or a 1-R-3-haloazetidine to yield an α-(1-R-3-azetidinyl)-α,α diphenylacetonitrile. The said acetonitrile derivative is then acid-hydrolyzed to α-(1-R-3-azetidinyl)-α,α-diphenylacetamide (III), which is a key starting material for a novel method for preparing the 3-methyleneazetidine compounds of the present invention.

In the said novel method, the α-(1-R-3-azetidinyl)-α,α-diphenylacetamide III is converted to a carbamate as in the stage of Hofmann reaction (Organic Reactions Vol. III, p. 282) by action of bromine and sodium methoxide or other alkali metal alkoxide in a suitable anhydrous solvent, preferably an alcohol, corresponding to the alcohol from which the alkali metal alkoxide is formed. The carbamate derivative II is converted to a present invention 3-methyleneazetidine compound I by the novel step of refluxing the carbamate in contact with a strong acid to eliminate the equivalent of an alkyl carbamate molecule.

Formulation of Pharmaceutical Compositions

In one of its embodiments, this invention provides a pharmaceutical composition adapted for alleviating the symptoms of depression in humans and other mammals. The pharmaceutical composition comprises a pharmaceutical carrier and an antidepressant quantity of a 3-methyleneazetidine compound corresponding to the formula:

wherein R is a lower-alkyl, cycloalkyl or phenyl-lower-alkyl radical.

The pharmaceutical compositions of the present invention are prepared in a form suitable for administering to a living animal.

Pharmaceutical compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate, and polyvinyl pyrrolidone.

For parenteral administration the carrier or excipient can be a sterile parenterally acceptable liquid (e.g., water) or a parenterally acceptable oil (e.g., arachis oil) contained in ampoules.

In compositions for rectal administration the carrier can comprise a suppository base such as cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage unit forms according to the invention. Each dosage unit adapted for oral administration may conveniently contain 10 to 40 mg of the active ingredient; each dosage unit adapted for intracardial or intravenous administration may conveniently contain 1 to 2 mg per cc of the active ingredient; whereas each dosage unit adapted for intramuscular administration may conveniently contain 5 to 10 mg per cc of the active ingredient.

Examples of compositions within the preferred ranges given are as follows:

A. Capsules

| Ingredients | Per capsule |
|---|---|
| 1. Active ingredient | 10.00 mg |
| 2. Lactose | 146.000 mg |
| 3. Magnesium stearate | 4.000 mg |

Procedure
1. Blend 1, 2 and 3.
2. Mill this blend and blend again.
3. This milled blend is then filled into #1 hard gelatin capsules.

B. Tablets

| Ingredients | Per Tablet, mg |
|---|---|
| 1. Active ingredient | 10.0 mg |
| 2. Corn starch | 20.0 mg |
| 3. Kelacid | 20.0 mg |
| 4. Keltose | 20.0 mg |
| 5. Magnesium stearate | 1.3 mg |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it though the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

C. Intravenous Injection

| Ingredients | Per ml |
|---|---|
| 1. Active ingredient | 1.0 mg |
| 2. pH 4.0 Buffer solution | qs to 1.0 ml |

Procedure
1. Dissolve the active ingredient in the buffer solution.
2. Aseptically filter the solution from step #1.
3. The sterile solution is now aseptically filled into sterile ampoules.
4. The ampoules are sealed under aseptic conditions.

D. Intramuscular Injection

| Ingredients | Per ml |
|---|---|
| 1. Active ingredient | 5.0 mg |
| 2. Isotonic buffer solution 4.0 | qs to 1.0 ml |

Procedure
1. Dissolve the active ingredient in the buffer solution.
2. Aseptically filter the solution from step #1.
3. The sterile solution is now aseptically filled into sterile ampoules.
4. The ampoules are sealed under aseptic conditions.

E. Suppositories

| Ingredients | Per Supp. |
|---|---|
| 1. Active ingredient | 10.0 mg |
| 2. Polyethylene Glycol 1000 | 1350.0 mg |
| 3. Polyethylene Glycol 4000 | 450.0 mg |

Procedure
1. Melt 2 and 3 together and stir until uniform.
2. Dissolve #1 in the molten mass from step #1 and stir until uniform.
3. Pour the molten mass from step #2 into suppository molds and chill.
4. Remove the suppositories from molds and wrap.

Although very small quantities of the active materials of the present invention are effective when minor therapy is involved or in cases of administration to subjects having a relatively low body weight, unit dosages are usually from 5 milligrams or above and preferably 25, 50 or 100 milligrams or even higher, depending of course upon the emergency of the situation and the particular result desired. Five to 50 milligrams appears optimum per unit dose, or usual broader ranges appear to be 1 to 100 milligrams per unit dose. Daily dosages should preferably range from 10 mg to 100 mg. The active ingredients of the invention may be combined with other pharmacologically active agents as stated above. It is only necessary that the active ingredient constitute an effective amount, i.e., such that a suitable effective dosage will be obtained consistent with the dosage form employed. Obviously, several unit dosage forms may be administered at about the same time. The exact individual dosages as well as daily dosages will, of course, be determined according to standard medical principals under the direction of a physician or veterinarian.

Antidepressant Activity of Invention Compounds

Antidepressant agents block many of the behavioral and physiological effects of tetrabenazine and reserpine, such as motor depression, hypothermia, and ptosis. Tetrabenazine is chemically related to reserpine which produces depression in humans (Davies, 1964)[1]. Because the onset of action of tetrabenazine is faster than that of reserpine, the former compound is more widely used as a tool for screening potential antidepressant drugs.

[1] Davies, E. D., Depression, Cambridge University Press, New York, 1964.

For the purpose of testing the antidepressant activity of present invention 3-methyleneazetidine compounds, five adult female mice (ICR-DUB strain) are given 20 mg/kg IP of test compound 30 minutes prior to the administration of a ptotic dose (32 mg/kg IP) of tetrabenazine (as the methane sulfonate salt). Thirty minutes later the presence or absence of complete eyelid closure (ptosis) is assessed in each animal.

For compounds which produced blockage of ptosis in all animals, and $ED_{50}$ value is obtained using a minimum of three geometrically spaced doses with five mice/dose. Protective $ED_{50}$ values are determined by probit analysis with 95% confidence limits and slope functions calculated by the method of Litchfield and Wilcoxon (1949)[2].

[2] Litchfield, J. T., Jr. and Wilcoxon, F. A simplified method of evaluating dose-effect experiments. J. Pharm. Exp. Ther. 96, 99–113, 1949.

Typical $ED_{50}$ values for reference antidepressent agents are shown in Table 1.

TABLE 1

| Blockade of Tetrabenazine-Induced Ptosis in Mice | |
|---|---|
| Compounds | $ED_{50}$ (95% Confidence Limits) Slope - mg/kg IP |
| imipramine (A. H. Robins) | 0.3 (0.1–0.6) 2.6 |
|  | 0.4 (0.2–0.9) 2.5 |
|  | 0.5 (0.2–1.2) 2.3 |
| viloxazine | 1.5 (0.7–3.2) 2.5 |

In accordance with the above described test and evaluation procedures, 1-isopropyl-3-diphenyleneazetidine oxalate has an $ED_{50}$ mg/kg (IP) of 2.18 (confidence limits, 1.18–4.03), and 1-methyl-3-diphenylmethyleneazetidine has an $ED_{50}$ mg/kg (IP) of 1.48 (confidence limits, 0.84–2.5).

Amphetamines and barbiturates are frequently useful in depression therapy, as well as tranquilizers. In particular, the use of tranquilizing drugs as with sedatives and the amphetamine group have shown valuable results especially with disturbed and agitated cases of depression. This invention is, therefore, intended to encompass the combined use of the foregoing with the antidepressant compounds thereof, as well as with other drugs used adjunctively in depression control and treatment. Thus, the compounds of this invention may be administered alone or in combination with other pharmacologically effective agents such as psychomotor stimulants, sedatives, tranquilizers and sedative-level dosages of tranquilizers, etc., as well as buffers and usual pharmaceutical carriers or diluents. Examples of some of these drugs are: phenobarbital, sodium phenobarbital, meprobamate, chlordiazepoxide hydrochloride, butaperazine, methamphetamine, amphetamine, and dextroamphetamine.

The following examples are illustrative of the preparation of present invention 3-methyleneazetidine compounds, and the synthesis of starting materials suitable for their preparation. The reactants and other specific ingredients are presented as being typical, and various modifications can be devised in view of the foregoing disclosure within the scope of the invention.

EXAMPLE 1

This example illustrates the preparation of 3-chloro-1-methylazetidine hydrochloride starting material:

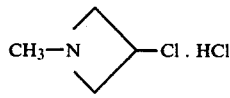

A mixture of dilute sodium hydroxide solution and 700 ml of toluene was used to partition 46 g (0.18 mole) of 3-diphenylmethoxy-1-methylazetidine oxalate. The toluene solution was dried over anhydrous sodium sulfate and further dried by azeotropic distillation of toluene to 300 ml final volume. The dried toluene solution was treated with 10% palladium-on-charcoal and hydrogenated at 45 psi at 80° C. for 5 hours. The mixture was filtered and 41 g (0.264 mole) of carbon tetrachloride was added to the filtrate. After cooling the resulting solution in an ice-methanol bath, 53.5 g (0.145 mole) of trioctylphosphine was added in one portion with stirring. The temperature rose rapidly to a maximum of 50° C. The solution was stirred for 30 minutes and distilled to a pot temperature of 150° C. The distillate was acidified with ethereal hydrogen chloride. The resulting crystals were separated by filtration and dried in vacuo, yielding 8.5 g of product (45%).

A solution of the base, 3-chloro-1-methylazetidine was prepared by partitioning 3-chloro-1-methylazetidine hydrochloride between toluene and dilute sodium hydroxide, drying the toluene solution with anhydrous sodium sulfate and passing the solution through a $\frac{3}{4}" \times 21"$ column of No. 4A molecular sieves.

EXAMPLE 2

This example illustrates the preparation of $\alpha,\alpha$-diphenyl-$\alpha$-(1-isopropyl-3-azetidinyl)acetonitrile starting material.

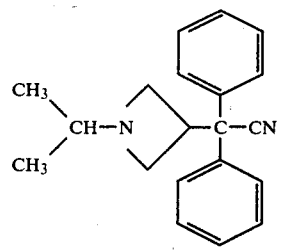

Procedure A. To 250 ml of triethylamine was added 114 g (0.4 mole) of 1-isopropyl-3-azetidinyl mesylate oxalate. About 250 ml of dry toluene was added followed by 77 g of anhydrous magnesium sulfate, and the mixture blended for about one minute and then filtered. The filtrate was added over a period of one hour to a refluxing mixture prepared by refluxing 18.5 g (0.44 mole) of 57% sodium hydride (in mineral oil) and 77.2 g (0.4 mole) of diphenylacetonitrile in 1500 ml of dry toluene for 3 hours. The mixture was refluxed for 2 hours, cooled and extracted with dilute hydrochloric acid. The organic layer was extracted five times with water and all the aqueous layers combined. The aqueous solution was made basic with sodium hydroxide and extracted with chloroform which was dried (sodium sulfate) and concentrated. The residue was crystallized from isooctane, yielding 68 g (58%) of product, m.p. 92°–95° C. Recrystallization from isooctane raised the melting point to 93°–95° C.

Analysis: Calculated for $C_{20}H_{22}N_2$: C,82.72; H,7.64; N,9.65;

Found: C,82.72; H,7.73; N,9.55.

Procedure B. A mixture of 40.42 g (0.96 mole) of 57% sodium hydride and 168 g (0.87 mole) of diphenylacetonitrile was refluxed in one liter of dry toluene for 3 hours. In a separate flask 100 g (0.87 mole) of methanesulfonyl chloride was added dropwise at 20° C. to a stirred solution of 100 g (0.87 mole) of 1-isopropyl-3-azetidinol and 101 g (1 mole) of triethylamine in 700 ml dry benzene. The mixture was stirred at 25° C. for 2 hours and filtered. The filter cake was washed with benzene. The combined filtrates were added dropwise over a period of about 30 minutes to the prepared refluxing suspension of the sodium salt of diphenylacetonitrile. After refluxing 1.5 hours, the cooled solution was washed with water and extracted with dilute hydrochloric acid followed by extraction with water. The aqueous extracts were combined, made basic with sodium hydroxide and extracted with chloroform. The chloroform solution was dried (sodium sulfate) and concentrated. The residue was crystallized from isooctane, yielding 142 g (56%) of product.

EXAMPLE 3

This example illustrates the preparation of α,α-diphenyl-α-(1-methyl-3-azetidinyl)acetonitrile starting material.

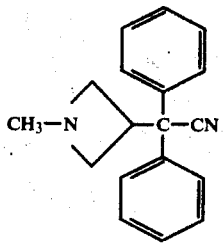

Procedure A. To 4 g (0.11 mole) sodium amide in 300 ml toluene was added 21 g (0.11 mole) of diphenylacetonitrile and the stirred mixture was refluxed in a nitrogen atmosphere for 4 hours. The heat was removed and a solution of 3-chloro-1-methylazetidine was added at a rate to maintain reflux. The solution was refluxed 4 hours, allowed to stand overnight, washed with water and extracted with dilute hydrochloric acid. The aqueous acid layer was made basic with dilute sodium hydroxide and extracted twice with isopropyl ether. The solution was dried (sodium sulfate) and concentrated. The residue was recrystallized from ligroin to yield 6.7 g (27%) of product, m.p. 113°–115° C.

Analysis: Calculated for $C_{18}H_{18}N_2$: C,82.41; H,6.92; N,10.68;

Found: C,82.31; H,6.98; N,10.51.

Procedure B. To 800 ml of ethanol was added 59 g (0.13 mole) of α,α-diphenyl-α-[1(1-phenylethyl)-3-azetidinyl] acetonitrile methobromide, 7.12 g (0.013 mole) of potassium hydroxide, and 0.25 g 10% palladium-on-charcoal. The mixture was shaken in a Parr hydrogenation apparatus at room temperature under an initial pressure of 45 psi of hydrogen for 24 hours. The mixture was filtered and the filtrate concentrated in vacuo. The residue was crystallized from isooctane. The yield of product was 21.7 g (64%), melting at 112°–115° C.

EXAMPLE 4

This example illustrates the preparation of α,α-diphenyl-α-(1-cyclohexyl-3-azetidinyl)acetonitrile starting material.

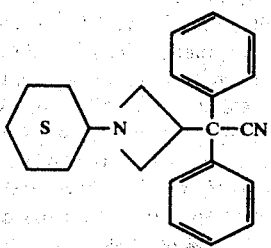

Methylene chloride containing 191 g (1.0 mole) of 1-cyclohexyl-3-azetidinol hydrochloride was extracted with dilute aqueous sodium hydroxide solution and the organic layer separated, dried over sodium sulfate, filtered and concentrated in vacuo. The residue was dissolved in dry benzene and mixed by stirring with 116 g (1.05 mole) of triethylamine and thereafter cooled with an ice bath. To the cold stirred solution was added dropwise 115 g of methanesulfonyl chloride and stirring was continued at room temperature for three hours and the mixture thereafter filtered. To one liter of dry toluene containing 50.0 g (1.0 mole) of sodium hydride was added at 45°–50° C., 193 g (1 mole) of diphenylacetonitrile and the mixture refluxed with stirring for two hours. To this stirred refluxing solution the foregoing filtrate was added at a fast dropwise rate. After addition was complete, reflux was continued for two hours and thereafter the solution was stirred overnight. An equivalent volume of isooctane was added and the solution extracted four times with dilute hydrochloric acid solution. The acid layers obtained in each extraction was combined, made basic with a mixture of 50% sodium hydroxide and ice and extracted with chloroform. The chloroform layer was dried, filtered and concentrated in vacuo. The residue as crystallized by adding isopropyl ether and thereafter the solid recrystallized from isopropyl ether to yield 58.0 g (18%) of produce melting at 111°–114° C.

Analysis: Calculated for $C_{23}H_{26}N_2$: C,83.59 H,7.93 N,8.48;

Found: C,83.24 H,7.94 N,8.27.

Following the same procedure, employing 1-ethyl-3-azetidinol hydrochloride instead of 1-cyclohexyl-3-azetidinol hydrochloride yields α,α-diphenyl-α-(1-ethyl-3-azetidinyl)acetonitrile.

EXAMPLE 5

This example illustrates the preparation of α,α-diphenyl-α-[1-(1-phenylethyl)-3-azetidinyl]acetonitrile starting material.

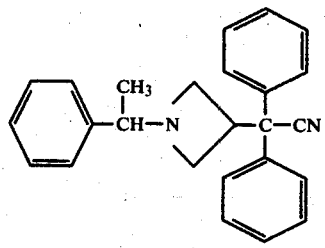

To a solution of 67.9 g (0.67 mole) of triethylamine and 114 g (0.64 mole) of 1-(1-phenylethyl)-3-azetidinol in 800 ml of dry benzene was added dropwise 73.6 g (0.65 mole) of methanesulfonyl chloride while cooling in an ice bath. After stirring two hours at room temperature the mixture was filtered. The filtrate was added dropwise over a 4-minute period to a refluxing suspension of the sodium salt of diphenyl-acetonitrile prepared by refluxing 123.5 g (0.64 mole) of the nitrile and 28.2 g (0.7 mole) of 57% sodium hydride in one liter of dry toluene for 2.5 hours. The toluene solution was extracted with dilute hydrochloric acid. The toluene-organic layer was treated with water and a volume of isooctane equal to the toluene layer. The oily layer and aqueous layer were separated together. The toluene layer was washed several times with water. All aqueous layers (and the oil) were combined and basified with dilute sodium hydroxide and extracted with chloroform. The chloroform layer was dried over sodium sulfate and concentrated by distillation. The residue was crystallized from isooctane isopropyl ether, yielding 94 g (42%) of product melting 122°–130° C.

Analysis: Calculated for C25H24N2: C,85.19; H,6.86; N,7.95; Found: C,84.98; H,6.84; N,7.83.

EXAMPLE 6

This example illustrates the preparation of α,α-diphenyl-α-[1-(1-phenylethyl)-3-azetidinyl]acetonitrile methobromide starting material.

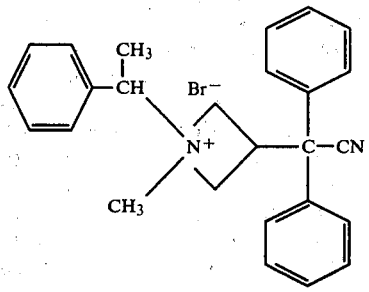

To 70 g (0.2 mole) of α,α-diphenyl-α-[1-(1-phenylethyl-3-azetidinyl]acetonitrile in 200 ml of isobutyl methyl ketone was added 17.5 g of methylbromide in 800 ml of the same solvent. The mixture was allowed to stand 4 days and filtered to give 65 g (72%) of product melting at 205°–208° C.

Analysis: Calculated for C26H27BrN2: C,69.79; H,6.08; N,6.26; Found: C,69.63; H,6.10; N,6.25.

EXAMPLE 7

This example illustrates the preparation of α,α-diphenyl-α-(1-methyl-3-azetidinyl)acetamide hydrochloride starting material.

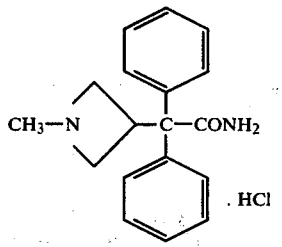

To 60 ml of concentrated sulfuric acid preheated to 60° C. was added 21.7 g (0.082 mole) of α,α-diphenyl-α-(1-methyl-3-azetidinyl)acetonitrile at a rate so as to maintain a temperature of 60°–70° C. The solution obtained was heated at 70° C. for 18 hours, poured on ice, made basic with 50% sodium hydroxide and extracted with chloroform. The chloroform extract was dried over sodium sulfate and concentrated and the residue crystallized from ethyl acetate-isopropyl alcohol to give 13.8 g of the free base (60%) melting at 171°–174° C. The base was treated with hydrogen chloride in isobutyl methyl ketone and the salt recrystallized from isopropyl alcohol, yielding 9 g of product melting at 182°–185° C.

Analysis: Calculated for C18H21ClN2O: C,68.24; H,6.68; N,8.84 Found: C,67.88; H,6.72; N,8.78.

EXAMPLE 8

This example illustrates the preparation of α,α-diphenyl-α-(1-isopropyl-3-azetidinyl)acetamide starting material.

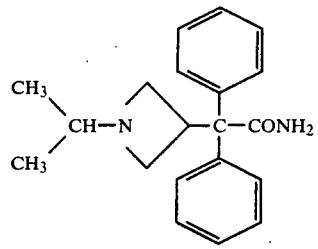

To 80 ml of concentrated sulfuric acid preheated to 70° C. was added 25 g (0.86 mole) of α,α-diphenyl-α-(1-isopropyl-3-azetidinyl)acetonitrile at a rate to maintain a temperature of 65°–75° C. The solution was heated at 70° C. for 18 hours and poured on ice. The mixture was made basic with 50% sodium hydroxide (while cooling with ice) and extracted with chloroform. The chloroform was dried (sodium sulfate) and concentrated. The residue was crystallized from ethyl acetate-ethanol to yield 15.7 g (59%) of product melting at 181°–184° C.

Analysis: Calculated for C20H24N2O1: C,77.89; H,7.84; N,9.08; Found: C,77.89; H,7.88; N,8.98.

Following the same procedure, employing α,α-diphenyl-α-(1-ethyl-3-azetidinyl)acetonitrile instead of the 1-isopropyl derivative yields α,α-diphenyl-α-(1-ethyl-3-azetidinyl)acetamide.

EXAMPLE 9

This example illustrates the preparation of α,α-diphenyl-α-[1-(1-phenylethyl)-3-azetidinyl]acetamide starting material.

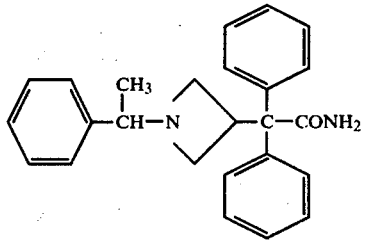

To 100 ml of concentrated sulfuric acid preheated to 70° C. was added with stirring, 50 g (0.142 moles) of α,α-diphenyl-α-[1-(1-phenylethyl)-3-azetidinyl]acetonitrile at a rate to maintain a temperature of 65°–70° C. The solution was heated at 72°–75° C. for 18 hours. The acid solution was poured onto ice and thereafter made basic with 50% aqueous sodium hydroxide solution and extracted with chloroform. The chloroform extract was dried over anhydrous sodium sulfate and concentrated by distillation. The residue was crystallized from isopropyl ether to give 28.5 g (54%) of material melting at 152°–153.5° C. A sample was recrystallized from isopropyl ether-isopropyl alcohol, yielding a product melting at 153°–154° C.

Analysis: Calculated for C25H26N2O: C,81.05; H,7.07; N,7.56; Found: C,80.83; ,7.07; N,7.40.

Following the same procedure, employing α,α-diphenyl-α-(1-cyclohexyl-3-azetidinyl)acetonitrile instead of the 1-phenylethyl derivative yields α,α-diphenyl-α-(1-cyclohexyl-3-azetidinyl)acetamide.

EXAMPLE 10

This example illustrates the preparation of 1-methyl-3-diphenylmethyleneazetidine.

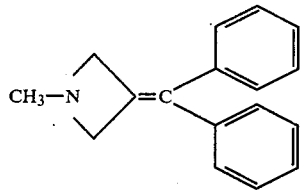

To 150 ml of methanol was added 4.6 g (0.20 mole) of sodium pellets, and upon dissolution, 14.0 g (0.05 mole) of α,α-diphenyl-α-(1-methyl-3-azetidinyl)acetamide was added. To this stirring suspension was added dropwise 16.0 g (0.10 mole) of liquid bromine, maintaining room temperature with ice-bath cooling. Stirring was continued for two hours. The solution was concentrated in vacuo, and the residue was treated with 100 ml of 6N sulfuric acid and refluxed for 18 hours. The acid mixture was made basic with sodium hydroxide and extracted with chloroform. The chloroform layer was dried, filtered, and concentrated in vacuo.

The residue was dissolved in isopropanol and treated with maleic acid, and the salt was recrystallized in isopropanol. The salt was partitioned between isopropyl ether and dilute sodium hydroxide. The ether was dried, filtered, and concentrated in vacuo. The residue was crystallized from isooctane, yielding 7.0 g, m.p. 93°-95° C.

Analysis: Calculated for $C_{17}H_{17}N$: C,86.76; H,7.28; N,5.95; Found: C,86.74; H,7.34; N,5.81.

Following the same procedure, employing the 1-ethyl derivative or the 1-cyclohexyl derivative in place of the 1-methyl derivatives, yields 1-ethyl-3-diphenylmethyleneazetidine and 1-cyclohexyl-3-diphenylmethyleneazetidine, respectively.

EXAMPLE 11

This example illustrates the preparation of 1-isopropyl-3-diphenylmethyleneazetidine oxalate.

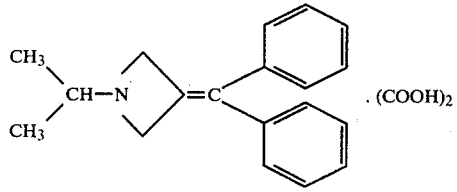

To 125 ml of methanol was added 18.1 g (0.336 mole) of sodium methoxide and 26 g (0.084 mole) of α,α-diphenyl-α-(1-isopropyl-3-azetidinyl)acetamide. To the stirred mixture was added dropwise 26.8 g (0.168 mole) of bromine over a period of 30 minutes, and the resulting solution was brought to reflux for 2 hours and concentrated. The residue was dissolved in 6N sulfuric acid and brought to reflux for 24 hours and extracted with isopropyl ether. The acid layer was made basic with sodium hydroxide and extracted with chloroform. The chloroform was dried ($Na_2SO_4$) and concentrated. The residue was treated with 0.08 mole of oxalic acid in ethanol. The resulting crystals were recrystallized three times from ethanol, yield 3 g (10%), m.p. 204°-205° C.

Analysis: Calculated for $C_{21}H_{23}N_1O_4$: C,71.36; H,6.56; N,3.96; Found: C,70.95; H,6.53; N,3.90.

Following the same procedure, employing the 1-phenylethyl derivative or the 1-(α-methylbenzyl) derivative instead of the 1-isopropyl derivative yields 1-phenylethyl-3-diphenylmethyleneazetidine oxalate and 1-(α-methylbenzyl)-3-diphenylmethyleneazetidine oxalate, respectively.

Following the procedure of Example 11 up to addition of oxalic acid, employing α,α-diphenyl-α-[1-(1-phenylethyl-3-azetidinyl]acetamide starting material yields 1-(α-methylbenzyl)-3-diphenylmethyleneazetidine.

What is claimed is:

1. 3-Methyleneazetidine compounds corresponding to the formula:

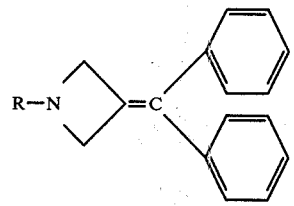

wherein R is a lower-alkyl radical and the pharmaceutically acceptable acid addition salts thereof.

2. A compound of claim 1 which is 1-methyl-3-diphenylmethyleneazetidine.

3. A compound of claim 1 which is 1-ethyl-3-diphenylmethyleneazetidine.

4. A compound of claim 1 which is 1-isopropyl-3-diphenylmethyleneazetidine.

5. A compound of claim 1 which is 1-isopropyl-3-diphenylmethyleneazetidine oxalate.

6. A pharmaceutical composition for the treatment of depression in humans comprising a pharmaceutical carrier and an antidepresant quantity of a 3-methyleneazetidine compound corresponding to the formula:

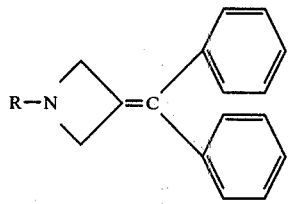

wherein R is a lower-alkyl radical and the pharmaceutically acceptable acid addition salts thereof.

7. A pharmaceutical composition in accordance with claim 6 wherein the 3-methylenediphenylazetidine compound is 1-isopropyl-3-diphenylmethyleneazetidine.

8. A pharmaceutical composition in accordance with claim 6 wherein the 3-methylenediphenylazetidine compound is 1-methyl-3-diphenylmethyleneazetidine.

9. A pharmaceutical composition in accordance with claim 6 wherein the 3-methylenediphenylazetidine compound is 1-isopropyl-3-diphenylmethyleneazetidine oxalate.

* * * * *